US005510118A

United States Patent [19]
Bosch et al.

[11] Patent Number: 5,510,118
[45] Date of Patent: Apr. 23, 1996

[54] PROCESS FOR PREPARING THERAPEUTIC COMPOSITIONS CONTAINING NANOPARTICLES

[75] Inventors: H. William Bosch, Bryn Mawr; Donna M. Marcera, Collegeville; Ronald L. Mueller, Downingtown; Jon R. Swanson, Macungie; Dinesh S. Mishra, Harleysville, all of Pa.

[73] Assignee: NanoSystems LLC, Collegeville, Pa.

[21] Appl. No.: 388,092

[22] Filed: Feb. 14, 1995

[51] Int. Cl.$^6$ ............................................. A61K 9/14
[52] U.S. Cl. .......................... 424/489; 424/488; 424/490
[58] Field of Search ............................... 424/488, 489, 424/490, 22

[56] References Cited

U.S. PATENT DOCUMENTS

| | | | |
|---|---|---|---|
| 4,107,288 | 8/1978 | Oppenheim et al. | 424/22 |
| 4,540,602 | 9/1985 | Motoyama et al. | 427/213.31 |
| 5,039,527 | 8/1991 | Tabibi et al. | 424/450 |
| 5,118,528 | 6/1992 | Fessi et al. | 427/213.36 |
| 5,145,684 | 9/1992 | Liversidge et al. | 424/489 |
| 5,228,905 | 7/1993 | Grunewalder et al. | 106/2 |
| 5,342,609 | 8/1994 | Meeh et al. | 424/9 |
| 5,399,363 | 3/1995 | Liversidge et al. | 424/490 |

OTHER PUBLICATIONS

Lachman et al, The Theory and Practice of Industrial Pharmacy, Chapter 2, "Milling", p. 45, (1986).

G. Gregoriadis, H. Da Silva, and A. T. Florence, "A Procedure for the Efficient Entrapment of Drugs in Dehydration-Rehydration Liposomes (DRVs)", Int. J. Pharm. 65, 235–242 (1990).

E. Doegito, H. Fessi, M. Appel, F. Puisieux, J. Bolard, and J. P. Devissaguet, "New Techniques for Preparing Submicronic Emulsions—Application to Amphotericine–B" STP Pharma Sciences 4, 155–162 (1994).

D. M. Lidgate, R. C. Fu, N. E. Byars, L. C. Foster, and J. S. Fleitman, "Formulation of Vaccine Adjuvant Muramyldipeptides. Part 3. Processing Optimization, Characterization and Bioactivity of an Emulsion Vehicle," Pharm Res. 6, 748–752 (1989).

H. Talsma, A. Y. Ozer, L. VanBloois, and D. J. Crommelin, "The Size Reduction of Liposomes with a High Pressure Homogenizer (Microfluidizer): Characterization of Prepared Dispersions and comparison with Conventional Methods," Drug Dev. Ind. Pharm. 15, 197–207 (1989).

D. M. Lidgate, T. Trattner, R. M. Shultz, and B. Maskiewicz, "Sterile Filtration of a Parenteral Emulsion," Pharm. Res. 9, 860–863 (1990).

R. Bomeier, and H. Chen, "Indomethacin Polymeric Nanosuspensions Prepared by Microfluidization," J. Contr. Rel. 12, 223–233 (1990).

R. Bodmeier, H. Chen, P. Tyle, and P. Jarosz, "Spontaneous Formation of Drug-Containing Acrylic Nanoparticles," J. Microencap, 8, 161–170 (1991).

F. Koosha, and R. H. Muller, "Nanoparticle Production by Microfluidization," Archiv Der Pharmazie 321, 680 (1988).

The Extra Pharmapoeia, by Martindale, 29th Edition, The Pharmaceutical Press, London, 1989.

*Primary Examiner*—Thurman K. Page
*Assistant Examiner*—William E. Benston, Jr.
*Attorney, Agent, or Firm*—Rudman & Balogh

[57] ABSTRACT

A process of preparing nanoparticulate drug substances comprising the steps of: preparing a premix of the drug substance and a surface modifier, and subjecting the premix to mechanical means to reduce the particle size of the drug substance, the mechanical means producing shear, impact, cavitation and attrition.

20 Claims, No Drawings

PROCESS FOR PREPARING THERAPEUTIC COMPOSITIONS CONTAINING NANOPARTICLES

BACKGROUND OF THE INVENTION

1. Field of the Invention

This invention relates to a process for preparing therapeutic compositions containing nanoparticles.

2. Reported Developments

Bioavailability is the degree to which a drug becomes available to the target tissue after administration. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. Poorly water soluble drugs, i.e., those having a solubility less than about 10 mg/ml, tend to be eliminated from the gastrointestinal tract before being absorbed into the circulation. Moreover, poorly water soluble drugs tend to be unsafe for intravenous administration techniques, which are used primarily in conjunction with fully soluble drug substances.

It is known that the rate of dissolution of a particulate drug can increase with increasing surface area, i.e., decreasing particle size. Consequently, methods of making finely divided drugs have been studied and efforts have been made to control the size and size range of drug particles in pharmaceutical compositions. For example, dry milling techniques have been used to reduce particle size and hence influence drug absorption. However, in conventional dry milling, as discussed by Lachman et al, *The Theory and Practice of Industrial Pharmacy*, Chapter 2, "Milling", p. 45, (1986), the limit of fineness is reached in the region of 100 microns (100,000 nm) when material cakes on the milling chamber. Lachman et al note that wet grinding is beneficial in further reducing particle size, but that flocculation restricts the lower particle size limit to approximately 10 microns (10,000 nm). However, there tends to be a bias in the pharmaceutical art against wet milling due to concerns associated with contamination. Commercial airjet milling techniques have provided particles ranging in average particle size from as low as about 1 to 50 µm (1,000–50,000 nm). However, such dry milling techniques can cause unacceptable levels of dust.

Other techniques for preparing pharmaceutical compositions include loading drugs into liposomes or polymers, e.g., during emulsion polymerization. However, such techniques have problems and limitations. For example, a lipid soluble drug is often required in preparing suitable liposomes. Further, unacceptably large amounts of the liposome or polymer are often required to prepare unit drug doses. Further still, techniques for preparing such pharmaceutical compositions tend to be complex. A principal technical difficulty encountered with emulsion polymerization is the removal of contaminants, such as unreacted monomer or initiator, which can be toxic, at the end of the manufacturing process.

U.S. Pat. No. 4,540,602 (Motoyama et al) discloses a solid drug pulverized in an aqueous solution of a water-soluble high molecular substance using a wet grinding machine. However, Motoyama et al teach that as a result of such wet grinding, the drug is formed into finely divided particles ranging from 0.5 µm (500 nm) or less to 5 µm (5,000 nm) in diameter.

EPO 275,796 describes the production of colloidally dispersible systems comprising a substance in the form of spherical particles smaller than 500 nm. However, the method involves a precipitation effected by mixing a solution of the substance and a miscible non-solvent for the substance and results in the formation of non-crystalline nanoparticles. Furthermore, precipitation techniques for preparing particles tend to provide particles contaminated with solvents. Such solvents are often toxic and can be very difficult, if not impossible, to adequately remove to pharmaceutically acceptable levels to be practical.

U.S. Pat. No. 4,107,288 describes particles in the size range from 10 to 1,000 nm containing a biologically or pharmacodynamically active material. However, the particles comprise a crosslinked matrix of macromolecules having the active material supported on or incorporated into the matrix.

U.S. Pat. No. 5,145,684 discloses a process for preparing particles consisting of a crystalline drug substance having a surface modifier or surface active agent adsorbed on the surface of the particles in an amount sufficient to maintain an average particle size of less than about 400 nanometers. The process of preparation comprises the steps of dispersing the drug substance in a liquid dispersion medium and applying mechanical means in the presence of grinding media to reduce the particle size of the drug substance to an average particle size of less than 400 nm. The particles can be reduced in the presence of a surface active agent or, alternatively, the particles can be contacted with a surface active agent after attrition. The presence of the surface active agent prevents flocculation/agglomeration of the nanoparticles.

The mechanical means applied to reduce the particle size of the drug substance is a dispersion mill, the variety of which include a ball mill, an attrition mill, a vibratory mill and media mill, such as sand mill, and a bead mill.

The grinding media for the particle size reduction is spherical or particulate in form and includes: $ZrO_2$ stabilized with magnesia, zirconium silicate, glass, stainless steel, titania, alumina and $ZrO_2$ stabilized with yttrium. Processing time of the sample can be several days long. This patent is incorporated herein in its entirety by reference.

To a more limited extent the prior art also utilized microfluidizers for preparing small particle-size materials in general. Microfluidizers are relatively new devices operating on the submerged jet principle. In operating a microfluidizer to obtain nanoparticulates, a premix flow is forced by a high pressure pump through a so-called interaction chamber consisting of a system of channels in a ceramic block which split the premix into two streams. Precisely controlled shear, turbulent and cavitational forces are generated within the interaction chamber during microfluidization. The two streams are recombined at high velocity to produce shear. The so-obtained product can be recycled into the microfluidizer to obtain smaller and smaller particles.

The prior art has reported two distinct advantages of microfluidization over conventional milling processes (such as reported in U.S. Pat. No. 5,145,684, supra): substantial reduction of contamination of the final product, and the ease of production scaleup.

Numerous publications and patents were devoted to emulsions, liposomes and/or microencapsulated suspensions of various substances including drug substances produced by the use of microfluidizers. See, for example:

1) U.S. Pat. No. 5,342,609, directed to methods of preparing solid apatite particles used in magnetic resonance imaging, x-ray and ultrasound.

2) U.S. Pat. No. 5,228,905, directed to producing an oil-in-water dispersion for coating a porous substrate, such as wood.

3) U.S. Pat. No. 5,039,527 is drawn to a process of producing hexamethylmelamine containing parenteral emulsions.

4) G. Gregoriadis, H. Da Silva, and A. T. Florence, "A Procedure for the Efficient Entrapment of Drugs in Dehydration-Rehydration Liposomes 0DRVs), *Int. J. Pharm.* 65, 235–242 (1990).

5) E. Doegito, H. Fessi, M. Appel, F. Puisieux, J. Bolard, and J. P. Devissaguet, "New Techniques for Preparing Submicronic Emulsions—Application to Amphotericine-B,: *STP Pharma Sciences* 4, 155–162 (1994).

6D. M. Lidgate, R. C. Fu, N. E. Byars, L. C. Foster, and J. S. Fleitman, "Formulation of Vaccine Adjuvant Muramyldipeptides. Part 3. Processing Optimization, Characterization and Bioactivity of an Emulsion Vehicle," Pharm Res. 6, 748–752 (1989).

7) H. Talsma, A. Y. Ozer, L. VanBloois, and D. J. Crommelin, "The Size Reduction of Liposomes with a High Pressure Homogenizer (Microfluidizer): Characterization of Prepared Dispersions and Comparison with Conventional Methods," *Drug Dev. Ind. Pharm.* 15, 197–207 (1989).

8) D. M. Lidgate, T. Tranner, R. M. Shultz, and R. Maskiewicz, "Sterile Filtration of a Parenteral Emulsion," *Pharm. Res.* 9, 860–863 (1990).

9) R. Bodmeier, and H. Chen, "Indomethacin Polymeric Nanosuspensions Prepared by Microfluidization," *J. Contr. Rel.* 12, 223–233 (1990).

10) R. Bodmeier, H. Chen, P. Tyle, and P. Jarosz, "Spontaneous Formation of Drug-Containing Acrylic Nanoparticles," *J. Microencap,* 8, 161–170 ( 1991).

11) F. Koosha, and R. H. Muller, "Nanoparticle Production by Microfluidization," *Archiv Der Pharmazie* 321, 680 (1988).

However, reports are few on reducing mean particle size (hereinafter sometimes abbreviated as MPS) of water-insoluble materials for use in pharmaceutical/diagnostic imaging compositions.

The present invention is directed to a process incorporating the advantages of microfluidizer process over conventional milling processes along with utilizing formulation and/or process parameters necessary for successful particle size reduction of a pharmaceutical suspension.

The primary forces attributed to microfluidization for producing either emulsions or dispersions, and for reducing the MPS of water-insoluble materials include: shear, involving boundary layers, turbulent flow, acceleration and change in flow direction; impact, involving collision of solid elements and collision of particles in the chamber of microfluidizer; and cavitation, involving an increased change in velocity with a decreased change in pressure and turbulent flow. An additional force can be attributed to conventional milling processes of attrition, i.e., grinding by friction. In reference to conventional milling process it is understood that the process involves the use of gravity, attrition and/or media mills, all containing a grinding media.

SUMMARY OF THE INVENTION

In accordance with the present invention, there is provided a process of preparing stable, dispersible, water-insoluble, drug nanoparticles consisting essentially of a crystalline drug substance having a surface modifier adsorbed on the surface thereof comprising the steps of:

a) dispersing a crystalline drug substance in a liquid dispersion medium containing a surface modifier, and b) subjecting the liquid dispersion medium to the comminuting action of a microfluidizer asserting shear, impact and cavitation forces onto the crystalline drug substance contained in the liquid dispersion medium for a time necessary to reduce the mean particle size of said crystalline drug substance to less than 400 nm.

The particles can be formulated into pharmaceutical compositions exhibiting remarkably high bioavailability.

This invention also provides a stable dispersion consisting essentially of a liquid dispersion medium and the above-described particles dispersed therein.

In a particularly valuable and important embodiment of the invention, there is provided a pharmaceutical composition comprising the above-described particles and a pharmaceutically acceptable carrier therefor. Such pharmaceutical composition is useful in a method of treating mammals.

It is an advantageous feature that a wide variety of surface modified drug nanoparticles free of unacceptable contamination can be prepared in accordance with this invention.

Still another advantageous feature of this invention is that pharmaceutical compositions containing poorly water soluble drug substances are provided which are suitable for intravenous administration techniques.

DETAILED DESCRIPTION OF THE INVENTION

This invention is based partly on the discovery that drug particles having an extremely small effective avenge particle size can be prepared by milling in a microfluidizer in conjunction with a surface modifier, and that such particles are stable and do not appreciably flocculate or agglomerate due to interparticle attractive forces and can be formulated into pharmaceutical compositions exhibiting unexpectedly high bioavailability. While the invention is described herein primarily in connection with its preferred utility, i.e., with respect to nanoparticulate drug substances for use in pharmaceutical compositions, it is also believed to be useful in other applications such as the formulation of particulate cosmetic compositions and the preparation of particulate dispersions for use in image and magnetic recording elements.

The particles of this invention comprise a drug substance. The drug substance exists as a discrete, crystalline phase. The crystalline phase differs from a non-crystalline or amorphous phase which results from precipitation techniques, such as described in EPO 275,796 cited above.

The Drug Substances

The invention can be practiced with a wide variety of drug substances. The drug substance preferably is present in an essentially pure form. The drug substance must be poorly soluble and dispersible in at least one liquid medium. By "poorly soluble" it is meant that the drug substance has a solubility in the liquid dispersion medium, e.g. water, of less than about 10 mg/ml, and preferably of less than about 1 mg/ml. A preferred liquid dispersion medium is water. However, the invention can be practiced with other liquid media in which a drug substance is poorly soluble and dispersible including, for example, aqueous salt solutions, safflower oil and solvents such as ethanol, t-butanol, hexane and glycol. The pH of the aqueous dispersion media can be adjusted by techniques known in the art.

Suitable drug substances can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobactefial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, corticosteroids, cough suppressants (expectorants and mucolytics), diagnostic agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anoretics, sympathomimetics, thyroid agents, vasodilators and xanthines. Preferred drug substances include those intended for oral administration and intravenous administration. A description of these classes of drugs and a listing of species within each class can be found in Martindale, *The Extra Pharmacopoeia,* Twenty-ninth Edition, The Pharmaceutical Press, London, 1989, the disclosure of which is hereby incorporated herein by reference in its entirety. The drug substances are commercially available and/or can be prepared by techniques known in the art.

Representative illustrative species of drug substances useful in the practice of this invention include:

17-α-pregno-2,4-dien-20-yno-[2,3-d]-isoxazol- 17-ol (Danazol);

5α,17α,- 1'-(methylsulfonyl)- 1'H-pregn-20-yno[3,2-c]-pyrazol- 17-ol (Steroid A);

piposulfam;

piposulfan;

camptothecin; and ethyl-3,5-diacetoamido-2,4-6- triiodobenzoate.

In particularly preferred embodiments of the invention, the drug substance is a steroid such as danazol or Steroid A or an antiviral agent.

Surface Modifiers

The particles of this invention contain a discrete phase of a drug substance as described above having a surface modifier adsorbed on the surface thereof. Useful surface modifiers are believed to include those which physically adhere to the surface of the drug substance but do not chemically bond to the drug.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate,carboxymethylcellulose calcium, carboxymethylcellulose sodium, methylcellulose, hyclroxyethylcellulose, hydroxypropylcellulose, hydroxypropylmethycellulose phthalate, noncrystalline cellulose, magnesium aluminum silicate, triethanolamine, polyvinyl alcohol (PVA), and polyvinylpyrrolidone (PVP). Most of these excipients are described in detail in the *Handbook of Pharmaceutical Excipients,* published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

Particularly preferred surface modifiers include polyvinyl pyrrolidone, Pluronic F68 and F108, which are block copolymers of ethylene oxide and propylene oxide, Tetronic 908, which is a tetrafunctional block copolymer derived from sequential addition of ethylene oxide and propylene oxide to ethylenediamine, dextran, lecithin, Aerosol OT, which is a dioctyl ester of sodium sulfosuccinic acid, available from American Cyanamid, Duponol P, which is a sodium lauryl sulfate, available from DuPont, Triton X-200, which is an alkyl aryl polyether sulfonate, available from Rohm and Haas, Tween 80, which is a polyoxyethylene sorbitan fatty acid ester, available from ICI Specialty Chemicals, Carbowax 3350 and 934, which are polyethylene glycols available from Union Carbide. Surface modifiers which have found to be particularly useful include polyvinylpyrrolidone, Pluronic F-68, and lecithin.

The surface modifier is adsorbed on the surface of the drug substance in an amount sufficient to maintain an effective average particle size of less than about 400 nm. The surface modifier does not chemically react with the drug substance or itself. Furthermore, the individually adsorbed molecules of the surface modifier are essentially free of intermolecular crosslinkages.

As used herein, particle size refers to a number average particle size of less than about 400 nm as measured by conventional particle size measuring techniques well known to those skilled in the art, such as sedimentation field flow fractionation, photon correlation spectroscopy, or disk centrifugation. By "effective average particle size of less than about 400 nm" it is meant that at least 90% of the particles have a weight average particle size of less than about 400 nm when measured by the above-noted techniques. In preferred embodiments of the invention, the effective average particle size is less than about 250 nm. In some embodiments of the invention, an effective average particle size of less than about 100 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than .400 nm.

The Microfluidizer

In the practice of the present invention the following microfluidizers were used, all supplied by Microfluidics International Corporation:

Model M110-EH, which is a laboratory scale microfluidizer which utilizes an electric hydraulic pump;

Model M-110Y, which is a laboratory scale microfluidizer equipped with a sanitary pressure transducer connected to a digital data acquisition system;

Model M-140K, which is a high pressure microfluidizer with a pressure limit of 40,000 psi; and Model M-210, which is a pilot plant microfluidizer with a pressure range from 3,000 to 30,000 psi, and with flow rates between 1.9 to 5.7 L/min. It is capable of handling a sample size of 3.8 L or greater.

As indicated, the primary forces attributed to microfluidization by the microfluidizer for producing either emulsions or dispersions, and for reducing mean particle size of water-insoluble materials are:

shear, involving boundary layers, turbulent flow, acceleration and change in flow direction;

impact, involving collision of the particles processed with solid elements of the microfluidizer, and collision between the particles being processed; and cavitation, involving an increased change in velocity with a decreased change in pressure, and turbulent flow.

An additional force can be attributed to attrition, i.e., grinding by friction.

The M-110Y laboratory scale microfluidizer consists of an air motor connected to a hydraulic pump which circulates the process fluid. The formulation stream is propelled at high pressures (up to 23,000 psi) through a specially designed interaction chamber which has fixed microchannels that focus the formulation stream and accelerate it to a high velocity. Within the chamber the formulation is subjected to intense shear, impact and cavitation, all of which contribute to particle size reduction. After processing, the formulation stream is passed through a heat exchanger coil and can be collected or recirculated through the machine. The microfluidizer was typically used in a continuous processing mode for up to three hour of total processing time. The heat exchanger and interaction chamber were externally cooled with a refrigerated circulating water bath.

The use of microfluidization in pharmaceutical dosage form development has largely been limited to processing of emulsions or liposomes as previously discussed.

The Process of Making the Nanoparticulates

A general procedure for preparing the particles useful in the practice of this invention follows. The drug selected is obtained commercially and/or prepared by techniques known in the art in a conventional coarse form. It is preferred, but not essential, that the particle size of the coarse drug substance selected be less than about 100 gm, as determined by sieve analysis. If the coarse particle size of the drug substance is greater than about 100 gm then it is preferred that the coarse particles of the drug substance be reduced in size to less than 100 gm using a conventional milling method such as airjet or fragmentation milling.

The coarse drug substance selected can then be added to a liquid medium in which it is essentially insoluble to form a premix. The concentration of the drug substance in the liquid medium can vary from about 0.1–60% w/w, and preferably is from 5–30% (w/w). It is preferred, but not essential, that the surface modifier be present in the premix. The concentration of the surface modifier can vary from about 0.1 to 90%; and preferably is 1–75%, more preferably 20–60%, by weight based on the total combined weight of the drug substance and surface modifier. The apparent viscosity of the premix suspension is preferably less than about 1000 centipoise.

The premix then can be transferred to the microfluidizer and circulated continuously first at low pressures, then at maximum capacity having a fluid pressure of from about 3,000 to 30,000 psi until the desired particle size reduction is achieved. The particles must be reduced in size at a temperature which does not significantly degrade the drug substance. Processing temperatures of less than about 30–40° C. are preferred.

There are two methods to collect a slurry and re-pass it in a microfluidizer. The "discreet pass" method collects every pass through the microfluidizer until all of the slurry has been passed through before re-introducing it again to the microfluidizer. This guarantees that every substance or particle has "seen" the interaction chamber the same amount of times. The second method recirculates the slurry by collecting it in a receiving tank and allowing the entire mixture to randomly mix and pass through the interaction chamber. We have found that recirculating a slurry is just as effective as the "discreet pass" method, however, maintaining slurry homogeneity in the receiving tank is important.

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of drug substance and surface modifier can vary widely and the optimal amount of the surface modifier can depend, for example, upon the particular drug substance and surface modifier selected, the critical micelle concentration of the surface modifier if it forms micelles, etc. The surface modifier preferably is present in an amount of about 0.1–10 mg per square meter surface area of the drug substance. The surface modifier can be present in an amount of 0.1–90%, preferably 20–60% by weight based on the total weight of the dry particle.

The resulting dispersion of this invention is stable and consists of the liquid dispersion medium and the above-described particles. The dispersion of surface modified drug nanoparticles can be spray coated onto sugar spheres or onto a pharmaceutical excipient in a fluid-bed spray coater by techniques well known in the art.

Pharmaceutical compositions according to this invention include the particles described above and a pharmaceutically acceptable carrier therefor. Suitable pharmaceutically acceptable carriers are well known to those skilled in the art. These include non-toxic physiologically acceptable carriers, adjuvants or vehicles for parenteral injection, for oral administration in solid or liquid form, for rectal administration, and the like. A method of treating a mammal in accordance with this invention comprises the step of administering to the mammal in need of treatment an effective amount of the above-described pharmaceutical composition. The selected dosage level of the drug substance for treatment is effective to obtain a desired therapeutic response for a particular composition and method of administration. The selected dosage level therefore, depends upon the particular drug substance, the desired therapeutic effect, on the route of administration, on the desired duration of treatment and other factors. As noted, it is a particularly advantageous feature that the pharmaceutical compositions of this invention exhibit unexpectedly high bioavailability as illustrated in the examples which follow. Furthermore, it is contemplated that the drug particles of this invention provide more rapid onset of drug action in oral applications and decreased gastric irritancy.

It is contemplated that the pharmaceutical compositions of this invention will be particularly useful in oral and parenteral, including intravenous, administration applications. It is expected that poorly water soluble drug substances, which prior to this invention, could not have been administered intravenously, may be administered safely in accordance with this invention. Additionally, drug substances which could not have been administered orally due to poor bioavailability may be effectively administered in accordance with this invention.

While applicants do not wish to be bound by theoretical mechanisms, it is believed that the surface modifier hinders the flocculation and/or agglomeration of the particles by functioning as a mechanical or steric barrier between the particles, minimizing the close, interparticle approach necessary for agglomeration and flocculation. Alternatively, if the surface modifier has ionic groups, stabilization by electrostatic repulsion may result. It was surprising that stable drug particles of such a small effective average particle size and free of unacceptable contamination could be prepared by the method of this invention.

Illustrative examples of drug substance microfluidized in the presence of surface active agents and mean particle size of the microfluidized drug substances are shown in Table I.

TABLE I

Microfluidization of Therapeutics

| Compound % w/w | Surfactant % w/w | Mean Particle Size |
|---|---|---|
| naproxen (2.5%) | HPMC (0.25%) | 309 nm (30 min) |
| | | 301 nm (60 min) |
| naproxen (2.5%) | HPMC (1.75%) | 335 nm (30 min) |
| | | 307 nm (60 min) |
| naproxen (20%) | HPMC (2.0%) | 314 nm (180 min) |
| naproxen (20%) | HPC (1.6%) | 223 nm (180 min) |
| naproxen (40%) | PVP K-29/32 (6%) | 271 nm (150 min) |
| WIN 49596 (20%) | SLS (0.2%) | 224 nm (60 min) |
| WIN 63394(6.8%) | F68 (5%) | 284 nm (30 min) |
| Danazol (12%) | DOSS (0.3%) | 318 nm (180 min) | wherein
naproxen = 6 methoxy-α-methyl-2-naphthaleneacetic acid
HPMC = hydroxypropylmethylcellulose
HPC = hydroxypropylcellulose
WIN 49596 = (5-α-, 17-α)-1'-(methylsulfonyl)-1'-H-preg-20-yno[3,2-C] pyrazol-17-ol (generic name zanoterone)
WIN 63394 = Benzoic acid, 6-dichloro-[6-methoxy-4-(1-methylethyl)-3-oxo-1,2-benzisothiazol-2-(3H)-yl]methyl S,S, dioxide
SLS = sodium lauryl sulfate
DOSS = sodium dioctylsulfosuccinate The invention has been described in detail with particular reference to certain preferred embodiments thereof, but it will be understood that variations and modifications can be effected within the spirit and scope of the invention.

What is claimed is:

1. A process for preparing particles consisting essentially of 99.9–10% by weight of a crystalline drug substance having a solubility in water of less than 10 mg/ml, said drug substance having a non-crosslinked surface modifier adsorbed on the surface thereof in an amount of 0. 1–90% by weight and sufficient to maintain an effective average particle size of less than about 400 nm, said process comprises the steps of:

a) preparing a promix of said crystalline drug substance having a particle size of less than about 100 μm and said surface modifier by mixing them in a liquid dispersion medium being selected form the group consisting of water, aqueous salt solutions, safflower oil, ethanol, t-butanol, hexane and glycol;

b) transferring said premix to a microfluidizer having an interaction chamber capable of producing shear, impact, cavitation and attrition forces;

c) subjecting said promix to said forces at a temperature not exceeding 40° C. and a fluid pressure of from about 3,000 to about 30,000 psi by passing said premix through said interaction chamber to reduce the particle size of said drug substance and to obtain a homogeneous slurry thereof:

d) collecting all the slurry from said interaction chamber into a receiving tank;

e) reintroducing said slurry m said receiving tank into said interaction chamber to further subject said slurry to said forces and thereby to decrease the effective average particle size of said drub substance: and f) repeating said collection and reintroduction steps until said drug substance is reduced to an effective average particle size of less than about 400 nm.

2. The process of claim 1 wherein said particles have an effective particle size of less than 250 nm.

3. The process of claim 1 wherein said particles have an effective particle size of less than 100 μm.

4. The process of claim 1 wherein said drug substance is selected from the group consisting of: analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, contrast media, corticosteroids, cough suppressants, diuretics, dopaminergics, haemostatics, immufiological agents, lipid regulating agents, muscle relaxants, parasympathomimetics, parathyroid calcitonin, prostaglandins, radio-pharmaceuticals, sex hormones, anti-allergic agents, stimulants, sympathomimetics, thyroid agents, vasoclilators and xanthines.

5. The process of claim 1 wherein said drug substance is a steroid.

6. The process of claim 1 wherein said said drug substance is selected from the group consisting of: (Danazol), 5α,17α,-1'-(methylsulfonyl)- 1'H-pregn-20-yno-pyrazol17-ol, piposulfam, piposulfan, camptothecin and ethyl-3,5-diacetoamido-2,4-6triiodobenzoate.

7. The process of claim 1 wherein said surface modifier is selected from the group consisting of: gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene caster oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone.

8. The process of claim 1 wherein said surface modifier is selected from the group consisting of: an ethylene oxide-propylene oxide block co-polymer, lecithin, an alkyl aryl polyether sulfonate, gum acacia, sodium dodecylsulfate, and a dioctylester of sodium sulfosuccinic acid.

9. A pharmaceutical composition comprising the particles prepared by the process of claim 1 in Combination with a pharmaceutically acceptable carrier.

10. A method of treating a mammal comprising the step of administering to the mammal an effective amount of the pharmaceutical composition of claim 9.

11. A process for preparing particles consisting essentially of 99.9–10% by weight of a crystalline drug substance having a solubility in water of less than 10 mg/ml, said drug substance having a non-crosslinked surface modifier adsorbed on the surface thereof in an amount of 0.1–90% by weight and sufficient to maintain an effective average particle size of less than about 400 nm, said process comprises the steps of:

a) preparing a promix of said crystalline drug substance having a particle size of less than about 100 μm and said surface modifier by mixing them in a liquid dispersion medium being selected form the group consisting of water, aqueous salt solutions, safflower oil, ethanol, t-butanol, hexane and glycol;

b) transferring said premix to a microfluidizer having an interaction chamber capable producing shear, impact, cavitation and attrition forces;

c) subjecting said premix to said forces at a temperature not exceeding 40° C. and a fluid pressure of from about 3,000 to about 30,000 psi by passing said premix through said interaction chamber to reduce the particle size of said drug substance and to obtain a homogeneous slurry thereof;

d) collecting a portion of the slurry from said interaction chamber into a receiving tank:

e) reintroducing said portion of the slurry into said interaction chamber; repeating said collection and reintroduction steps in a continuous process until said drug substance is reduced to an effective average particle size of less than about 400 nm.

12. The process of claim 11 wherein said particles have an effective particle size of less than 250 nm.

13. The process of claim 11 wherein said particles have an effective particle size of less than 100 μm.

14. The process of claim 11 wherein said drug substance is selected from the group consisting of: analgesics, anti-inflammatory agents, anthelmintics, anti-arrhythmic agents, antibiotics, antic oagul ants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, contrast media, corticosteroids, cough suppressants, diuretics, dopaminergics, haemostatics, immuriological agents, lipid regulating agents, muscle relaxants, parasympathomimetics, parathyroid calcitonin, prostaglandins, radio-pharmaceuticals, sex hormones, anti-allergic agents, stimulants, sympathomimetics, thyroid agents, vasodilators and xanthines.

15. The process of claim 11 wherein said drug substance is a steroid.

16. The process of claim 11 wherein said drug substance is selected from the group consisting of: (Danazol), 5α, 17α,- 1'-(methylsulfonyl)- 1'H-pregn-20-yno-pyrazol-17-ol, piposulfam, piposulfan, camptothecin and ethyl-3,5-diacetoamido-2,4-6-triiodobenzoate.

17. The process of claim 11 wherein said surface modifier is selected from the group consisting of: gelatin, casein, locithin, gum acacia, cholesterol, tragaeanth, stearic acid, benzalkonium chloride, calcium stearate, glyccryl monostearate, cetostearyl alcohol, cetomacrogol emulsifying wax, sorbitan esters, polyoxyethylcne alkyl ethers, polyoxyethylene caster oil derivatives, polyoxyethylene sorbitan htty acid esters, polyethylene glycols, polyoxyethylcne stearates, colloidel silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone.

18. The process of claim 11 wherein said surface modifier is selected from the group consisting of: an ethylene oxide-propylene oxide block co-polymer, lecithin, an alkyl aryl polyether sulfonate, gum acacia, sodium dodecylsulfate, and a dioctylester of sodium sulfosuccinic acid.

19. A pharmaceutical composition comprising the particles prepared by the process of claim 11 in combination with a pharmaceutically acceptable carrier.

20. A method of treating a mammal comprising the step of administering to the mammal an effective amount of the pharmaceutical composition of claim 19.

* * * * *